United States Patent
Shimomura

(10) Patent No.: US 10,262,848 B2
(45) Date of Patent: Apr. 16, 2019

(54) MASS SPECTROMETER

(71) Applicant: SHIMADZU CORPORATION, Kyoto-shi, Kyoto (JP)

(72) Inventor: Manabu Shimomura, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 9 days.

(21) Appl. No.: 15/544,737

(22) PCT Filed: Jan. 21, 2015

(86) PCT No.: PCT/JP2015/051516
§ 371 (c)(1),
(2) Date: Jul. 19, 2017

(87) PCT Pub. No.: WO2016/117053
PCT Pub. Date: Jul. 28, 2016

(65) Prior Publication Data
US 2018/0012740 A1 Jan. 11, 2018

(51) Int. Cl.
H01J 49/00 (2006.01)
H01J 49/04 (2006.01)
(Continued)

(52) U.S. Cl.
CPC .......... *H01J 49/0009* (2013.01); *G01N 27/62* (2013.01); *H01J 49/0409* (2013.01); *H01J 49/0422* (2013.01); *G01N 30/7206* (2013.01)

(58) Field of Classification Search
CPC .............. H01J 49/0009; H01J 49/0409; G01N 30/7206
(Continued)

(56) References Cited

U.S. PATENT DOCUMENTS

| 2006/0071159 A1* | 4/2006 | Hashimoto | G01N 27/622 250/287 |
| 2008/0265152 A1* | 10/2008 | Bateman | B01D 59/44 250/283 |
| 2015/0323500 A1* | 11/2015 | Davis | G01N 27/624 250/281 |

FOREIGN PATENT DOCUMENTS

JP 2002-039993 A 2/2002

OTHER PUBLICATIONS

International Search Report for PCT/JP2015/051516 dated Mar. 17, 2015 [PCT/ISA/210].
(Continued)

*Primary Examiner* — Nicole M Ippolito
(74) *Attorney, Agent, or Firm* — Sughrue Mion, PLLC

(57) ABSTRACT

In a device adjustment process, when a solenoid valve is opened, a gas resulting from vaporization of PFTBA held in a container is drawn into an ion source, a relationship between ambient temperature and a correction coefficient for actual signal values is experimentally determined beforehand. In an actual adjustment process, an ambient temperature acquirer reads the ambient temperature and refers to the correction information to determine the correction coefficient corresponding to the ambient temperature at that moment. A signal value corrector multiplies an actually measured peak area value by the correction coefficient to correct the actual signal value. A device adjustment controller adjusts a voltage applied to an ion detector so that the corrected actual signal value matches with a reference signal value. The voltage applied to the ion detector can be thereby adjusted so that the detector has the same level of gain independent of the ambient temperature.

4 Claims, 2 Drawing Sheets

(51) Int. Cl.
*G01N 30/72* (2006.01)
*G01N 27/62* (2006.01)

(58) Field of Classification Search
USPC .................................. 250/281, 282, 283, 288
See application file for complete search history.

(56) References Cited

OTHER PUBLICATIONS

Written Opinion dated Mar. 17, 2015 in application No. PCT/JP2015/051516.

\* cited by examiner

| AMBIENT TEMPER-ATURE | INTRODUCTION AMOUNT OF STANDARD SAMPLE GAS | DETECTOR VOLTAGE (DETECTOR GAIN) AFTER NORMAL ADJUSTMENT | DIRECTION OF CORRECTION OF ACTUAL SIGNAL VALUE | DIRECTION OF CORRECTION OF REFERENCE SIGNAL VALUE |
|---|---|---|---|---|
| LOW | SMALL | HIGH | ↑ | ↓ |
| MEDIUM | MEDIUM | MEDIUM | — | — |
| HIGH | LARGE | LOW | ↓ | ↑ |

MASS SPECTROMETER

CROSS REFERENCE TO RELATED APPLICATIONS

This application is a National Stage of International Application No. PCT/JP2015/051516, filed on Jan. 21, 2015, the contents of all of which are incorporated herein by reference in their entirety.

TECHNICAL FIELD

The present invention relates to a mass spectrometer, and particularly to a mass spectrometer which can suitably be combined with a gas chromatograph so as to be used as a gas chromatograph mass spectrometer.

BACKGROUND ART

In general, gas chromatograph mass spectrometers (which are hereinafter called the "GC-MS") need to regularly or irregularly undergo adjustment and calibration processes using standard samples in order to maintain high levels of accuracy and sensitivity for measurements. A popularly used standard sample for the adjustment of a mass spectrometer in a GC-MS is PFTBA (perfluorotributylamine) which is comparatively inexpensive as well as easy to handle.

Patent Literature 1 discloses a configuration of a standard sample supply unit in a conventionally and commonly used GC-MS, which is used for introducing a standard sample, such as PFTBA, into the mass spectrometer in place of a sample gas eluted from the column of the gas chromatograph. Specifically, the GC-MS described in the document includes a container for holding a solution of the standard sample, such as PFTBA, and a standard sample introduction pipe one end of which connected to the upper portion of the container via a solenoid valve. The other end of the pipe is either directly connected to the ion source, or connected via a T-joint to a sample supply passage which connects the exit port of the column and the ion source.

In a GC-MS, the ion source of the mass spectrometer is placed within an analysis chamber maintained in a high-vacuum state by evacuation with a vacuum pump. Therefore, the ion source and the sample supply passage connected to it are also internally maintained at a reduced pressure level. Accordingly, in the aforementioned standard sample supply unit, when the solenoid valve connected to the standard sample container is opened, a standard sample gas resulting from vaporization of the standard sample held in the container is drawn through the standard sample introduction pipe into the ion source. In the adjustment process of the mass spectrometer, while the standard sample gas is introduced into the ion source in this manner, either a scan measurement, or a selected ion monitoring (SIM) measurement in which a standard sample component is selected as the target, is performed to acquire data.

In a typical procedure for adjusting a mass spectrometer in a GC-MS, voltages applied to such elements as the lens electrode for converging ions are adjusted so as to maximize the area value (or height value) of the peak corresponding to the PFTBA on the obtained mass chromatogram, i.e. so as to maximize detection sensitivity. Voltages applied to the quadrupole mass filter are also adjusted so that the pattern of the peaks appearing on the mass spectrum corresponding to the PFTBA becomes as similar as possible to that of a standard mass spectrum previously prepared for PFTBA. Subsequently, a voltage applied to the ion detector, such as a secondary electron multiplier, is adjusted so that the actual signal value, such as the peak area value corresponding to the PFTBA on the mass chromatogram, will match with a reference value. By adjusting the applied voltage to the ion detector, i.e. the gain of the ion detector, in this manner so that the real signal value for a standard sample of a known concentration matches with the reference value, it is possible improve the reproducibility of the measurement.

However, the previously described type of conventional GC-MS has the following problem.

The introduction amount of PFTBA drawn from the standard sample container into the ion source (per unit time) during the adjustment of the mass spectrometer is considerably dependent on not only the gas pressure (degree of vacuum) within the ion source but also the surrounding temperature (i.e. ambient temperature), since the standard sample container is placed under ambient temperature and the volatilization volume of the PFTBA considerably varies with the ambient temperature. A variation in the amount of introduction of the PFTBA into the ion source causes a considerable fluctuation in the amount of ions generated from the PFTBA within the ion source, which consequently changes the actually obtained signal value even with the same voltage applied to the ion source. As a result, as in the case of the summer and winter seasons, when there are large seasonal differences in the ambient temperature, the gain of the detector becomes also different and causes a variation in the sensitivity despite the effort of adjusting the applied voltage to make the actual signal value match with the same reference value. Therefore, for example, it will be difficult to accurately compare a measured result obtained in the summer season with one obtained in the winter season.

CITATION LIST

Patent Literature

Patent Literature 1: JP 2002-39993 A

SUMMARY OF INVENTION

Technical Problem

One possible method for solving the aforementioned problem is to control the temperature of the standard sample container so as to prevent this container from being affected by the changing ambient temperature so that the standard sample gas will be constantly introduced into the ion source at a fixed rate. However, such a method inevitably makes the device complex in structure, requiring an additional cost. The standard sample supply unit is indeed an important component that affects measurement accuracy and other capabilities of the device. However, expending a high amount of cost for this unit is normally difficult since this unit is often offered as an accessory or optional product and not integrated in the main measurement unit.

The present invention has been developed to solve such problems. Its objective is to provide a mass spectrometer capable of securing high levels of reproducibility and accuracy for measurements by performing the device adjustment with high accuracy even when the amount of standard sample gas introduced into the ion source changes due to the ambient temperature.

Solution to Problem

The present invention developed for solving the previously described problem is a mass spectrometer including:

an ion source for generating ions originating from a sample component; a mass separator for separating ions generated by the ion source according to their mass-to-charge ratios; an ion detector for detecting ions separated by the mass separator; a standard sample container for holding a standard sample; a standard sample supply passage for connecting the standard sample container and the ion source; and a passage-switching section provided on the standard sample supply passage, for switching the passage between a state in which the communication between the standard sample container and the ion source through the passage is allowed and a state in which the communication is blocked, the mass spectrometer having the function of adjusting a relevant section of the mass spectrometer while a standard sample gas originating from the standard sample is introduced through the standard sample supply passage into the ion source, and the mass spectrometer including:

a) a temperature detector for measuring the ambient temperature around the mass spectrometer;

b) a correction information storage section for previously storing correction information which shows, or is based on, a relationship between the ambient temperature and the amount of standard sample gas introduced into the ion source; and c) a device adjustment executer for performing a device adjustment using the standard sample gas, by measuring the ambient temperature with the temperature detector, retrieving the correction information corresponding to the measured ambient temperature from the correction information storage section, and performing the device adjustment using a signal value corrected with the correction information.

The mass spectrometer according to the present invention may be singly used, although the device is typically combined with a gas chromatograph so as to be used as a gas chromatograph mass spectrometer.

In the mass spectrometer according to the present invention, for example, device manufacturers experimentally investigate the relationship between the ambient temperature and the amount of standard sample gas introduced into the ion source, or the relationship between the temperature and an actual signal value obtained by a measurement for a standard sample component under the same conditions except for the ambient temperature, or a similar relationship. Based on the result, correction information which shows, or is based on, the relationship between the ambient temperature and the amount of standard sample gas introduced into the ion source is prepared and stored in the correction information storage section. For example, the correction information may be the deviation of the introduction amount of gas from an introduction amount of the standard sample gas at a reference ambient temperature, deviation of the signal value from an actual signal value obtained under the introduction amount of the standard sample gas at a reference ambient temperature, or correction coefficient calculated for correcting those deviations. Needless to say, the device may additionally be provided with the function of allowing users rather than the device manufacturers to prepare correction information and store it in the storage section.

In response to a command from a user (analysis operator) or similar signal, the device adjustment using the standard sample gas is conducted by the device adjustment executer as follows: Initially, the ambient temperature at that point in time is measured with the temperature detector, and the correction information corresponding to the measured ambient temperature is retrieved from the correction information storage section. Concurrently, the passage-switching section is operated so as to switch to the state in which the standard sample container can communicate with the ion source through the standard sample supply passage, allowing the standard sample gas to be drawn through the standard sample gas passage into the ion source. In this state, a mass spectrometric analysis for the standard sample component in the gas is performed. The actual signal values obtained by this analysis are used to perform the adjustment of each relevant section of the device. More specifically, the actual signal values or reference signal value used as the reference for the adjustment is corrected with the retrieved correction information corresponding to the ambient temperature at that point in time, and those corrected actual signal values or reference signal value is used in the device adjustment. Thus, the difference in the amount of standard sample gas introduced into the ion source due to the difference in the ambient temperature is reflected in the device adjustment, allowing the device adjustment to be performed without being affected by the aforementioned difference, i.e. as if the amount of standard sample gas introduced into the ion source were maintained at a fixed level.

As one preferable mode of the mass spectrometer according to the present invention, the device adjustment executer may be configured to adjust the gain of the ion detector by adjusting a voltage applied to the same detector so that the actual signal value corresponding to the standard sample gas matches with a predetermined reference signal value, and to correct either the actual signal value or the reference signal value based on the correction information.

For this configuration, suppose that the correction as in the mass spectrometer according to the present invention is not performed. In this case, when the ambient temperature is relatively high and a large amount of standard sample gas is introduced into the ion source, the amount of ions generated within the ion source will accordingly increase, so that the gain of the ion detector will be set at a lower level than in the case where the ambient temperature is relatively low. By comparison, in the case of the mass spectrometer according to the present invention, when, for example, the ambient temperature is relatively high and a large amount of standard sample gas is introduced into the ion source, the device corrects, based on the correction information, either the actual signal values to lower levels or a reference signal value to a higher level. Consequently, the gain of the ion detector will set at a higher level than in the case where no such correction is made, which reduces the variation in the detection sensitivity due to the difference in the ambient temperature.

The standard sample is not limited to any specific kind. When the ion source is an ion source which employs electron ionization, PFTBA is normally used as the standard sample. PFTBA shows a significant change in gas volatilization volume for a temperature change around ordinary temperature (approximately 25° C.). For such a sample, reducing the influence of the ambient-temperature change based on the correction information in the previously described manner is particularly effective.

Advantageous Effects of the Invention

In the mass spectrometer according to the present invention, the device adjustment can be appropriately performed so as to obtain high levels of reproducibility and accuracy for measurements regardless of the ambient temperature at the installation site of the device, i.e. without being affected by a seasonal difference (e.g. summer or winter), on/off state of the air conditioning, or other environmental factors.

Accordingly, with the mass spectrometer according to the present invention, it is possible to accurately compare, for example, a result obtained by a measurement in the summer season with one obtained in the winter season.

DESCRIPTION OF EMBODIMENTS

Figure 1:
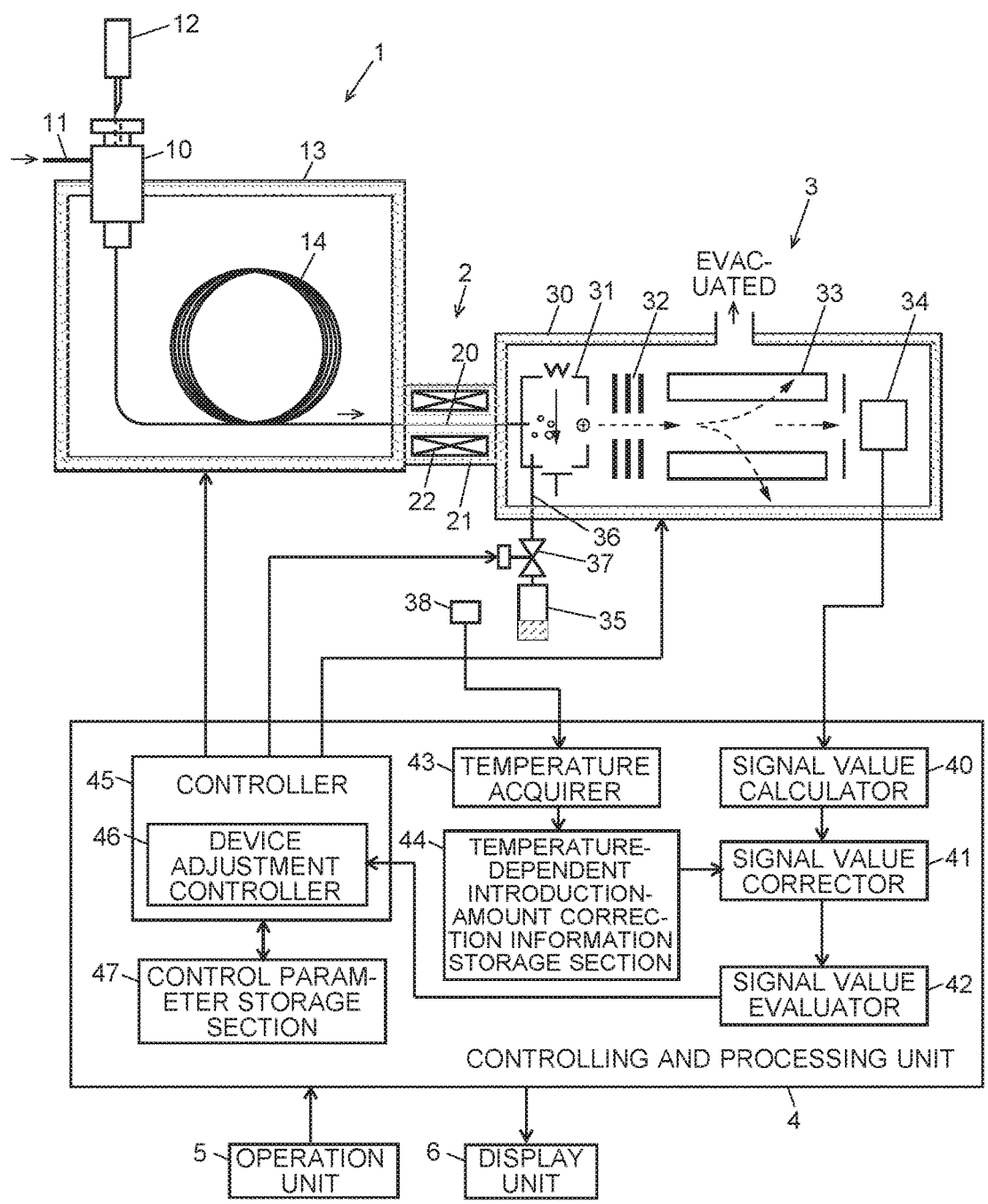
FIG. 1 is a configuration diagram showing the main components of a GC-MS system as one embodiment of the present invention.

A GC-MS system using a mass spectrometer as one embodiment of the present invention is hereinafter described with reference to the attached drawings. FIG. 1 is a configuration diagram showing the main components of the GC-MS system of the present embodiment.

In a gas chromatograph 1, a column (capillary column) 14 is contained in a column oven 13 for controlling the temperature of the column 14. At the entrance port of this column 14, a sample vaporization chamber 10 is provided. A carrier gas, which is supplied through a carrier gas passage 11 to the sample vaporization chamber 10 at a substantially fixed flow rate, is passed through this chamber 10 into the column 14. With the stream of carrier gas thus formed, when a trace amount of liquid sample is injected from a microsyringe 12 into the sample vaporization chamber 10, the liquid sample immediately vaporizes and is carried by the stream of carrier gas into the column 14. The configuration shown in FIG. 1 is a "split-less" configuration. It is also possible to use a "split" configuration in which a portion of the sample gas is discharged through a split passage to the outside.

The sample components in the sample gas sent into the column 4 are temporally separated while passing through the column 14. A GC/MS interface 2 provided between the gas chromatograph 1 and the mass analyzer 3 includes a sample supply passage 20 for supplying the sample gas and a heater block 21 with an embedded heater 22 for controlling the temperature of the sample supply passage 20. The sample gas flowing from the exit port of the column 14 passes through the sample supply passage 20 whose temperature is controlled by the heater block 21, to be introduced into an ion source 31 in the mass analyzer 3.

In the mass analyzer 3, a lens electrode 32, quadrupole mass filter 33, ion detector 34 and other elements along with the ion source 31 are placed within a vacuum chamber 30 which is maintained in a high-vacuum state by being evacuated with a vacuum pump (not shown). The ion source 31 is an electron ionization source having a thermion-generating filament, trapping electrode and other elements. The components contained in the sample gas introduced through the sample supply passage 20 are ionized by this ion source 31. Due to the effect of an electric field, the generated ions are extracted from the ion source 31, converged by the lens electrode 32 and introduced into the quadrupole mass filter 33. A voltage produced by a superposition of direct and radiofrequency voltages is applied to the quadrupole mass filter 33, allowing only an ion having a specific mass-to-charge ratio corresponding to the applied voltage to pass through the longitudinal space in the quadrupole mass filter 33 and reach the ion detector 34.

The ion detector 34, which includes a conversion dynode, secondary electron multiplier and other elements, produces electric signals corresponding to the amounts of incident ions. Those signals are fed to a controlling and processing unit 4, in which the signals are converted into digital signals and processed by a predetermined method, so as to create a mass spectrum, mass chromatogram, total ion chromatogram or similar form of information as well as to perform various analyzing tasks, such as qualitative and quantitative analyses.

For the adjustment of the relevant sections in the mass analyzer 3, or more specifically, for the adjustment of the voltage applied to the lens electrode 32, voltage applied to quadrupole mass filter 33, voltage applied ion detector 34 as well as other relevant variables, the mass spectrometer 3 is provided with a standard sample supply unit which includes: a PFTBA container 35 holding PFTBA as the standard sample; a solenoid valve 37 connected to the upper portion of the container 35; and a standard sample introduction pipe 36 with one end connected to the solenoid valve 37 and the other end connected to the inside of the ion source 31.

The GC-MS system of the present embodiment also includes an ambient temperature sensor 38 at an appropriate location, e.g. on the outer casing of the device.

The controlling and processing unit 4 is responsible for controlling relevant sections for data processing and measurement tasks. It includes a signal value calculator 40, signal value corrector 41, signal value evaluator 42, ambient temperature acquirer 43, temperature-dependent introduction-amount correction information storage section 44, controller 45, control parameter storage section 47 and other functional blocks. The controller 45 includes a device adjustment controller 46. Connected to the controlling and processing unit 4 are an operation unit 5 for allowing users to appropriately perform operations or give commands, and a display unit 6 for showing analysis results and other information. An example of the temperature-dependent introduction-amount correction information storage section 44 is a flash memory, in which correction information (which will be described later) is stored at an appropriate point in time before the device is delivered to the user.

The controlling and processing unit 4 may be configured using a personal computer as a hardware resource, with its functional blocks embodied by running, on that personal computer, a dedicated controlling and processing software program previously installed on the same computer.

Figures 2, 3:
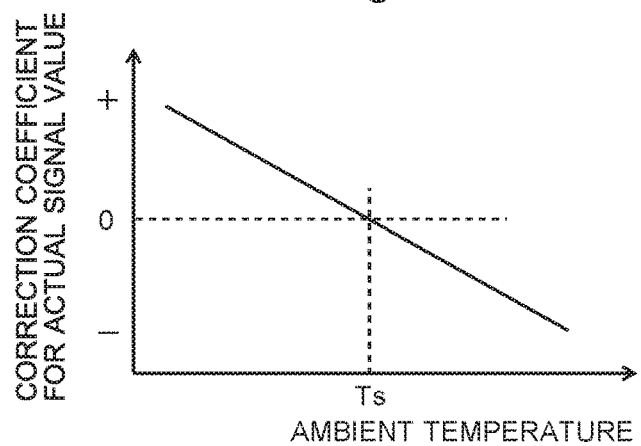
FIG. 2 is a table explaining the difference in the injection amount of the standard sample gas depending on the ambient temperature and its correction strategy in the GC-MS system of the present embodiment.
FIG. 3 is a graph showing a schematic relationship between the ambient temperature and a correction coefficient for actual signal values in the GC-MS system of the present embodiment.

The GC-MS system of the present embodiment is characterized by the "auto-tuning" operation for automatically adjusting the mass analyzer 3. This auto-touring operation is hereinafter described with reference to FIGS. 2 and 3 in addition to FIG. 1. FIG. 2 is a table explaining the difference in the injection amount of the standard sample gas depending on the ambient temperature and its correction strategy. FIG. 3 is a graph showing a schematic relationship between the ambient temperature and a correction coefficient for actual signal values.

When an analysis operator using the operation unit 5 issues a command to perform the auto-tuning of the mass analyzer 3, the device adjustment controller 46 opens the solenoid valve 37 and controls the relevant sections of the mass analyzer 3 to perform a mass spectrometric analysis according to a predetermined algorithm.

The ion source 31 is placed within the vacuum chamber 30 maintained in a high-vacuum state. Therefore, the inside of the ion source 31 is also maintained at a reduced pressure level. When the solenoid valve 37 is opened to allow the PFTBA container 35 to communicate with the ion source 31 through the standard sample introduction pipe 36, the PFTBA gas volatilized from the PFTBA solution in the PFTBA container 35 is drawn into the ion source 31. The PFTBA molecules in the drawn gas come into contact with the thermions and become ionized. The resulting ions are converged by the lens electrode 32 and introduced into the quadrupole mass filter 33. Needless to say, in this process, no liquid sample is injected into the sample vaporization chamber 10; the carrier gas is solely supplied through the sample supply passage 20 to the ion source 31.

With the PFTBA being introduced into the ion source 31 in the previously described manner, the adjustment of the voltage applied to the lens electrode 32, adjustment of the voltage applied to the quadrupole mass filter 33 and other adjustments are initially performed. Those adjustments are performed in the same manner as conventionally done, and therefore, will not be described.

After the adjustments of the voltages applied to the lens electrode 32 and quadrupole mass filter 33 as well as other tasks are completed, the adjustment of the voltage applied to the ion detector 34 is performed. This adjustment is hereinafter described.

As described earlier, while the solenoid valve 37 is in the open state, the PFTBA gas is drawn into the ion source 31, and the introduction amount of this gas changes with the ambient temperature, since the volatilization volume of the gas from the PFTBA solution depends on the ambient temperature. As shown in FIG. 2, when the ambient temperature is high, the amount of standard sample gas (PFTBA gas) introduced into the ion source 31 is larger than when the ambient temperature is low. The amount of ions originating from PFTBA generated within the ion source 31 also becomes larger, so that an accordingly larger amount of ions will reach the ion detector 34. In the case of adjusting the voltage applied to the lens electrode 32, the applied voltage is adjusted so as to maximize the area value of the peak on a mass chromatogram obtained by an SIM measurement in which an ion originating from PFTBA is selected as the target. Therefore, a difference in the peak area value due to a difference in the ambient temperature does not affect the adjustment.

On the other hand, the voltage applied to the ion detector 34 is a parameter which determines the gain of this detector 34; the higher the applied voltage is, the higher the gain becomes. Setting the gain too high causes a signal saturation in the ion detector 34 in a measurement of a high-concentration sample, while setting the gain too low may make the detector unable to detect a low-concentration sample. Therefore, the gain of the ion detector 34 needs to be properly set. To this end, the adjustment of the voltage applied to the ion detector 34 is performed to make the peak area value for the PFTBA match with a reference signal value specified by the device manufacturer or other organizations. In such an adjustment process, when the ambient temperature is high and a large amount of ions originating from PFTBA reach the ion detector 34, the applied voltage is decreased since the gain of the ion detector 34 needs to be lowered. Consequently, as shown in FIG. 2, when the ambient temperature is relatively high, the gain of the ion detector 34 will be lower than when the ambient temperature is relatively low. This means that the measurement sensitivity varies depending on the ambient temperature when a measurement is performed for an unknown sample having the same concentration.

To avoid this problem, a correction process taking into account the ambient temperature is performed when adjusting the voltage applied to the ion detector 34.

Specifically, when the ambient temperature is high, the correction should be made in the direction in which the peak area value calculated from the measured mass chromatogram decreases, i.e. in which the actual signal value decreases, because, as explained earlier, when the ambient temperature is high, the amount of ions originating from the PFTBA and reaching the ion detector 34 is larger than when the ambient temperature is low. Conversely, when the ambient temperature is low, the correction should be made in the direction in which the actual signal value increases. In FIG. 2, those directions are indicated by the up and down arrows. Correction coefficients for maintaining the corrected actual signal values at a substantially fixed level over a predetermined range of ambient temperatures can be experimentally determined beforehand. Therefore, for example, the manufacturer of the present device experimentally determines the relationship between the ambient temperature and the correction coefficient for the actual signal value, and stores data based on the experimental result in the temperature-dependent introduction-amount correction information storage section 44.

For example, those data represent a relationship as shown in FIG. 3, in which the correction coefficient, with its value at the reference ambient temperature Ts defined as zero, has positive values within the temperature range lower than Ts (i.e. the correction increases the actual signal value) and negative values within the temperature range higher than Ts (i.e. the correction decreases the actual signal value). It should be noted that the correction coefficient and the ambient temperature do not always have a linear relationship, as in FIG. 3.

When the voltage applied to the ion detector 34 is to be actually adjusted, the ambient temperature acquirer 43 reads the ambient temperature measured with the ambient temperature sensor 38 at that point in time and determines the correction coefficient corresponding to the ambient temperature at that point in time by referring to the correction information stored in the temperature-dependent introduction-amount correction information storage section 44. Meanwhile, the signal value calculator 40 creates a mass chromatogram based on the detection signals obtained with the ion detector 34 through the SIM measurement and calculates the area value of the peak corresponding to the PFTBA on that mass chromatogram. When the ambient temperature is comparatively high, the peak corresponding to the PFTBA becomes large in size, and the peak area value also becomes large.

Next, the signal value corrector 41 multiplies the calculated peak area value by the correction coefficient determined from the temperature-dependent introduction-amount correction information storage section 44, to obtain the corrected peak area value. When the ambient temperature is higher than the reference ambient temperature Ts, the correction coefficient has a negative value and the peak area value is decreased by the value based on the correction coefficient. The signal value evaluator 42 compares the corrected peak area value with a preset reference peak area value (reference signal value) and feeds the comparison result back to the device adjustment controller 46. Based on the feedback, the device adjustment controller 46 operates a detector voltage generator (not shown) to change the amount of voltage applied to the ion detector 34. By this operation, the gain of the ion detector 34 changes, which leads to a change in the peak area value corresponding to the PFTBA.

By such a feedback control, the device adjustment controller 46 adjusts the voltage applied to the ion detector 34 so that the difference between the corrected peak area value and the reference peak area value in the signal value evaluator 42 becomes smaller than a predetermined value. When the difference between the corrected and reference peak area values has become smaller than the predetermined value, the device adjustment controller 46 stores the value of the applied voltage at that point in time in the control parameter storage section 47. This value will be used as a control parameter in the subsequent measurement for an unknown sample.

Since the actual signal values are properly corrected according to the ambient temperature at that point in time, the gain of the ion detector 34 can be adjusted at a substantially fixed, optimal level independent of the ambient temperature. Therefore, even when there is a difference in the ambient temperature, measurements results for an unknown sample can be obtained under almost the same level of gain, and those measurement results can be accurately compared.

In the previous embodiment, the peak area value obtained by a mass spectrometric analysis of PFTBA, i.e. the actual signal value, is corrected according to the ambient temperature. It should be easy to conceive the idea that, instead of the actual signal value, the reference signal value to be compared with the actual signal value may be corrected according to the ambient temperature to obtain a similar effect. As shown in FIG. 2, in the case of correcting the reference signal value, the correction of should be made in the opposite direction to the correction of the actual signal value: When the ambient temperature is high, the correction should be made in the direction in which the reference peak area value, i.e. the reference signal value, increases. When the ambient temperature is low, the correction should be made in the direction in which the reference signal value decreases.

The previous embodiment is concerned with the case in which PFTBA, which is most popularly used in GC-MS, is used as the standard sample. It is evident that the present invention can also be applied in the case of using a different kind of standard sample. However, depending on the vapor pressure or other properties of the compound, a change in the ambient temperature may not cause any significant change in the introduction amount of gas under the gas pressure within the ion source. From this point of view, PFTBA can be considered to be one of the compounds for which the present invention can produce particular effects, since the introduction amount of the PFTBA gas significantly changes with a change in the ambient temperature.

It is also evident that the previous embodiment is a mere example of the present invention, and any change, addition or modification can be appropriately made to it within the spirit of the present invention.

REFERENCE SIGNS LIST

1 . . . Gas Chromatograph
10 . . . Sample Vaporization Chamber
11 . . . Carrier Gas Passage
12 . . . Microsyringe
13 . . . Column Oven
14 . . . Column
2 . . . GC/MS Interface
20 . . . Sample Supply Passage
21 . . . Heater Block
22 . . . Heater
3 . . . Mass Analyzer
30 . . . Vacuum Chamber
31 . . . Ion Source
32 . . . Lens Electrode
33 . . . Quadrupole Mass Filter
34 . . . Ion Detector
35 . . . PFTBA Container
36 . . . Standard Sample Introduction Pipe
37 . . . Solenoid Valve
38 . . . Ambient Temperature Sensor
4 . . . Controlling and Processing Unit
40 . . . Signal Value Calculator
41 . . . Signal Value Corrector
42 . . . Signal Value Evaluator
43 . . . Ambient Temperature Acquirer
44 . . . Temperature-Dependent Introduction-Amount Correction Information Storage Section
45 . . . Controller
46 . . . Device Adjustment Controller
47 . . . Control Parameter Storage Section
5 . . . Operation Unit
6 . . . Display Unit

The invention claimed is:

1. A mass spectrometer including: an ion source for generating ions originating from a sample component; a mass separator for separating ions generated by the ion source according to their mass-to-charge ratios; an ion detector for detecting ions separated by the mass separator; a standard sample container for holding a standard sample; a standard sample supply passage for connecting the standard sample container and the ion source; and a passage-switching section provided on the standard sample supply passage, for switching the passage between a state in which a communication between the standard sample container and the ion source through the passage is allowed and a state in which the communication is blocked, the mass spectrometer having a function of adjusting a section of the mass spectrometer while a standard sample gas originating from the standard sample is introduced through the standard sample supply passage into the ion source, and the mass spectrometer comprising:
   a) a temperature detector for measuring an ambient temperature around the mass spectrometer;
   b) a correction information storage section for storing correction information which shows, or is based on, a relationship between the ambient temperature and an amount of standard sample gas introduced into the ion source; and
   c) a device adjustment executer for performing a device adjustment using the standard sample gas, by measuring the ambient temperature with the temperature detector, retrieving the
   correction information corresponding to the measured ambient temperature from the correction information storage section, and performing the device adjustment using a signal value corrected with the correction information.

2. The mass spectrometer according to claim 1, wherein:
   the section of the mass spectrometer that is adjusted is the ion detector; and
   the device adjustment executer adjusts a gain of the ion detector by adjusting a voltage applied to the same detector so that an actual signal value corresponding to the standard sample gas matches with a predetermined reference signal value, and to correct either the actual signal value or the reference signal value based on the correction information.

3. The mass spectrometer according to claim 2, wherein:
the standard sample is perfluorotributylamine.

4. The mass spectrometer according to claim 1, wherein:
the standard sample is perfluorotributylamine.

* * * * *